United States Patent
Julliard et al.

[11] Patent Number: 5,913,234
[45] Date of Patent: Jun. 15, 1999

[54] SPECTROSCOPIC METHOD AND APPARATUS

[75] Inventors: Karin Julliard, Lausanne; Nicolas Gisin, Geneva; Jean-Paul Pellaux, Geneva, all of Switzerland

[73] Assignee: Orbisphere Laboratories Neuchatel S.A., Neuchatel, Switzerland

[21] Appl. No.: 08/954,466

[22] Filed: Oct. 20, 1997

[30] Foreign Application Priority Data

Nov. 5, 1996 [EP] European Pat. Off. ............. 96810734

[51] Int. Cl.$^6$ .................................................. G01N 21/17
[52] U.S. Cl. ..................... 73/24.02; 73/61.49; 73/61.79; 250/339.13; 356/51; 356/436; 356/437
[58] Field of Search .............................. 73/24.01, 24.02, 73/31.01, 31.02, 31.03, 61.49, 61.79, 64.53; 250/339.13, 341.7, 343; 356/51, 432, 436, 437

[56] References Cited

U.S. PATENT DOCUMENTS

| 3,948,345 | 4/1976 | Rosencwaig . | |
|---|---|---|---|
| 4,028,932 | 6/1977 | Rosencwaig . | |
| 4,436,428 | 3/1984 | Watanabe et al. . | |
| 4,457,162 | 7/1984 | Rush et al. ............................ | 73/24.01 |
| 4,557,137 | 12/1985 | Kitamori et al. ...................... | 73/61.79 |
| 4,594,004 | 6/1986 | Ishida et al. ......................... | 73/24.02 X |
| 4,641,973 | 2/1987 | Nestler et al. ........................ | 250/343 X |
| 4,738,536 | 4/1988 | Kitamori et al. ...................... | 356/432 |
| 5,408,327 | 4/1995 | Geiler et al. . | |

FOREIGN PATENT DOCUMENTS

| 0590813 | 4/1994 | European Pat. Off. . |
|---|---|---|
| 085728 | 12/1995 | European Pat. Off. . |
| 42 23 337 | 1/1994 | Germany . |
| 44 11 853 | 10/1995 | Germany . |

Primary Examiner—Daniel S. Larkin
Attorney, Agent, or Firm—Blank Rome Comisky & McCauley LLP

[57] ABSTRACT

A method and apparatus for determining the concentration of a substance of interest by gas-coupled photoacoustic spectroscopy (GC-PAS) with an essentially monochromatic beam of radiation in an optical portion of the electromagnetic spectrum; the radiation is selected so as to be absorbed by the substance of interest and the beam is modulated at a sonic frequency which is sufficiently high for generating a primary signal that depends upon the absorption coefficient of the substance of interest as well as upon parameters of operating the method; in order to compensate for these operating parameters, the beam is additionally modulated at a sonic frequency which is sufficiently low for generating a secondary signal which does not depend upon the absorption coefficient of the substance of interest, but, depends only upon parameters of operating the method; a ratio of the first and the second signal is obtained to generate a compensated signal for determining the concentration of the substance of interest.

13 Claims, 3 Drawing Sheets

SPECTROSCOPIC METHOD AND APPARATUS

BACKGROUND OF THE INVENTION

This invention generally relates to method and apparatus means for analyzing substances by spectroscopy and, specifically, to the so-called gas-coupled photoacoustic (GC-PAS herein) spectroscopy.

PRIOR ART

GC-PAS is a method discovered more than a hundred years ago; it has been reviewed during the last few decades, and provides an alternative to more widely used spectroscopic techniques, such as transmission or reflectance spectroscopy. GC-PAS is particularly suited for analysis of strongly absorbing liquids or solids.

The effect underlying GC-PAS is well described by a theory of Rosencwaig and Gersho (RG theory) which states that the pressure waves in the coupling gas are produced by transfer of heat from the periodically irradiated sample into the contacting gas. Periodical irradiation in this context refers to exposure of the sample to a modulated or pulsating light beam where the modulation of pulse frequency is in the audio or sonic range of, typically about 10–100'000 Hz. The term "modulated beam" is used herein to refer to a beam modulated in the sonic frequency range. Practical applications of the theory have been disclosed, inter alia, in U.S. Pat. No. 3,948,345 to Rosencwaig.

Briefly, the principle of the GC-PAS effect in terms of the RG theory is as follows: the liquid or solid sample is enclosed in a cell with a transparent gas and is irradiated by modulated light. Then, optical absorption by the sample gives rise to a temperature increase in the absorption zone. One part of the produced heat propagates to the surrounding gas leading to a pressure increase. A sound wave at the sonic modulation frequency of the light is produced, and its amplitude is proportional to the amount of energy which is transferred from the absorbing zone to the contact gas. This will be illustrated in more detail below (FIG. 1).

Generally, GC-PAS technique presents several advantages in comparison with other spectroscopic techniques because it allows one to study opaque samples without the need for very thin cells that are easily obstructed, and does not require special sample preparations. However, one disadvantage of this technique is that the GC-PAS effect depends on many operating parameters which are highly susceptible to fluctuation, such as mean pressure, temperature, gas volume, gas composition, microphone sensitivity, and, of course, light intensity.

OBJECTS AND SUMMARY OF THE INVENTION

An important object of the present invention is a GC-PAS method and apparatus suitable for scientific as well as industrial application, including, but not restricted to, on-line analyses of process fluids, e.g. for monitoring glucose and sucrose concentrations in water in the context of beverage processing, which method and apparatus are independent of the above mentioned fluctuating parameters and provide for long time stability, reproducibility of measurement, and good signal precision, notably when analyzing liquids under conditions where the levels of the liquid tend to fluctuate in the GC-PAS cell during measurements so that neither the pressure inside the cell nor the gas volume can be kept sufficiently constant to provide for reliable operation when using conventional apparatus and method means. Further, the invention aims at a possibility to use cost effective light sources, typically commercial $CO_2$ lasers without costly power stabilization.

These objects and further advantages will be achieved, according to a first embodiment of the invention, by a method for determining the concentration of a substance of interest by GC-PAS with an essentially monochromatic beam of radiation in an optical portion of the electromagnetic spectrum, wherein the radiation is selected so as to be absorbed by the substance of interest, and wherein the beam is modulated at a sonic frequency which is sufficiently high for generating a signal (termed primary signal herein) that depends essentially upon the absorption coefficient of the substance of interest as well as upon parameters of operating the method; the method according to the invention is characterized in that:

(a) the beam is additionally modulated at a sonic frequency which is sufficiently low for generating an additional or secondary signal which does not depend upon the absorption coefficient of the substance of interest, but depends only upon parameters of operating the method; and that (b) a ratio of the primary and the secondary signal is formed to generate a compensated signal for determining the concentration of the substance of interest. The compensated signal obtained by the inventive method is essentially independent of temperature, gas volume, gas pressure, and light intensity of the source of the beam.

According to a second general embodiment, the invention provides for a GC-PAS apparatus suitable for determining the concentration of a substance of interest; the apparatus comprises:

(A) a source for producing at least one essentially monochromatic beam of a radiation in an optical portion of the electromagnetic spectrum, wherein the radiation is selected so as to be absorbed by the substance of interest;

(B) a cell for receiving the substance of interest; the cell is operatively connected with a sonic detector for generating an output;

(C) means for modulation of the monochromatic beam at sonic frequencies;

(D) means for receiving the output from the sonic detector and for evaluating said output to produce a signal dependent upon the concentration of the substance of interest;

according to the invention, the apparatus is characterized in that the means (C) for modulation comprises:

(C1) a first modulating means for imparting to the monochromatic beam at least one primary modulation frequency at which the output produced by the sonic detector is a primary signal dependent upon the absorption coefficient of the substance of interest and upon parameters of operating the apparatus, and (C2) a second modulating means for imparting to the monochromatic beam at least one secondary modulation frequency at which the output produced by the sonic detector is a secondary signal substantially not dependent upon the absorption coefficient of the substance of interest but only upon the parameters of operating the apparatus;

and that the means (D) for receiving and evaluating include:

(D1) means for processing the output produced by the sonic detector so as to recover said primary signal and said secondary signal; and (D2) means for deriving, from a ratio between said primary signal and said secondary signal, a compensated signal that is dependent upon the absorption coefficient of the substance of interest, but not dependent upon the parameters of operating the apparatus.

PREFERRED EMBODIMENTS OF THE INVENTION

Preferably, the radiation used in the inventive method is selected so as to be strongly absorbed by the undiluted substance of interest; for many purposes of the invention, the substance of interest, or sample, preferably is substantially opaque to the radiation used, i.e. absorbs more than 99% of the radiation that penetrates into the sample under the conditions of operating the inventive method or apparatus.

The radiation should be in the optical portion of the electromagnetic spectrum; this includes visible as well as ultraviolet and infrared radiation, say electromagnetic radiation within a frequency range of from about $3*10^{-10}$ to about $3*10^{-15}$ Hz; selection of an appropriate frequency will primarily depend upon the absorption coefficient of the substance of interest, i.e. the sample should be strongly absorbing, but selection may also depend upon availability of suitable light sources and optical systems. Frequencies of visible light as well as radiation in the IR and UV ranges are preferred for many purposes of the invention.

Further, while polychromatic radiation and a suitable filter could be used for producing an essentially monochromatic radiation, laser-type light sources are preferred; commercially available lasers, such as $CO_2$ lasers, represent a typical example of a suitable light source. Selection of a suitable sensor is within the capacity of those experienced in the art and is not assumed to be a critical aspect of the invention.

The cell for generating a GC-PAS signal can be of any type; again, selection of a suitable cell is within the capacity of those experienced in the art and, again, this is not believed to be an aspect of novelty. Generally, such a cell comprises a body or housing for receiving the sample material, a window to allow passage of the monochromatic light beam, at least one microphone, and at least one port to allow passing the sample into and out of the cell. Suitable cells, or cell components, including microphones are available commercially and are disclosed, e.g., in EP-A-0 685 728 and the art referenced therein.

By the same token, means for modulating the beam in a sonic frequency range are known in the art. A generally preferred modulator is a so-called chopper, i.e. a rotating body, such as an indented or perforated disk, which interrupts the beam by physically intervening in the path of the beam. However, non-mechanical interruption of the beam could be used for modulation in the sonic frequency range, e.g. by periodic switching off and on of the light source.

According to the invention, at least one additional modulation is used for producing at least one secondary modulation in addition to the primary modulation. The same type of modulator may be used for the primary and the secondary modulation, but it is within the scope of the invention to use different types of modulators provided that they are capable of generating different pulsing frequencies. Again, selection of a particular construction of the modulating means, such as choppers, is within the competence of persons skilled in the art.

According to the best knowledge of applicants, neither the use of two or more modulating means, such as choppers, nor the use of at least two differing modulation frequencies in the audio range, nor—of course—the advantages resulting therefrom have been disclosed in the art, and the use of at least two modulating means, or choppers, and at least two different modulation frequencies are believed to be the crucial feature of novelty herein.

The first or primary modulation, or modulating means, e.g. chopper, is selected to generate a first or primary modulation frequency at which the GC-PAS signal produced in the cell is essentially dependent upon the absorption coefficient of the sample material, as well as parameters of operating the method, or apparatus, respectively, and a first or primary signal component is generated by the sonic detector or sensor, e.g. a microphone. This will be explained in more detail below, and specific examples of such frequencies for specific sample materials will be provided for illustration.

The secondary modulating means, e.g. chopper, will generate a second or secondary modulation frequency at which the GC-PAS signal produced by the cell is essentially not dependent upon the absorption coefficient of the sample material, but only upon the above parameters of operation which are not specific for the sample material but specific for the operating conditions. Thus, a secondary signal component is generated by the sonic detector; the reasons for this requirement will be explained in more detail below, and specific examples of such frequencies for specific sample material will be given.

As is conventional per se, the signal or output produced by the sonic detector, e.g. microphone, can be processed, e.g. amplified and/or transformed, if needed or desired in a manner known per se. Preferably, both the primary as well as the secondary output of the sonic detector are processed by means of so-called "lock-in amplifiers" known for use in measuring minute signals buried in random noise and surrounded by large discrete interfering frequencies. Examples are ITHACO®, DYNATRAC®, and lock-in amplifiers of the type supplied by Stanford Research, e.g. models SR510 and SR530, with a frequency range of 0.5 Hz to 100 kHz.

Suitable means for calculating the ratio of the signal components can be hard wired circuits or computer programs, the latter being preferred if additional parameters are to be included when producing the final output signal. e.g. a digital indication of the concentration of a specific substance of interest.

The invention is applicable to detecting, measuring, or monitoring all those substances of interest that can be detected, measured, or monitored by prior art GC-PAS methods and apparatus; this includes liquids as well as solids.

BRIEF DESCRIPTION OF THE DRAWINGS

The invention will now be explained in more detail with reference to the attached formula sheet and the drawings in which.

DETAILED EXPLANATION OF THE DRAWINGS

Figure 1:
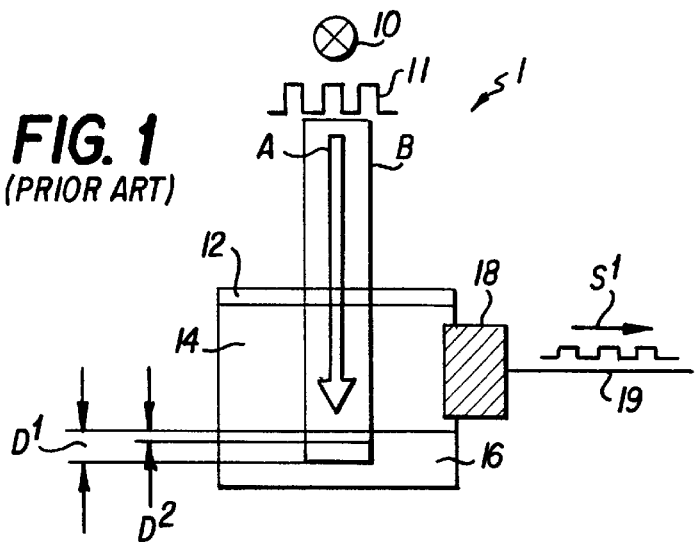
FIG. 1 is a diagram to illustrate the principle of the GC-PAS effect.

FIG. 1 is a diagrammatic view of a GC-PAS apparatus 1, according to the prior art for illustrating the principle of the GC-PAS method. Apparatus 1 comprises a source 10 for monochromatic radiation which is modulated by a modulating means, such as a chopper or other type of optical or optomechanical modulation means, to produce a beam B with a square-wave intensity curve and passing in the direction of arrow A through a window 12 into cell 14 containing a transparent gas.

Optical absorption of the radiation by the solid or liquid sample layer 16 gives rise to a brief temperature increase in the absorption zone. One part of the produced heat propagates to the surrounding gas and generates a brief pressure increase, or pulse. A sound wave at the modulation frequency of the light is produced in this manner, and its amplitude is proportional to the amount of energy which is transferred from the absorbing zone of sample 16 to the contact gas within cell 14. The sound so generated is detected by a microphone 18 which produces an electrical signal $S^1$ that is passed out from the detector via line 19 into an evaluating device (not shown in FIG. 1).

Two dimensions of particular interest are indicated in FIG. 1 as $D^1$ and $D^2$, respectively: $D^1$ corresponds to parameter $l_\alpha$ while $D^2$ corresponds with $\mu_s$ as used in equations (1) and (2) shown in the formula sheet and discussed below.

In order to quantify GC-PAS, two sample parameters can be introduced and will be used herein: the absorption length dimension indicated in FIG. 1 as $D^1$ and the thermal diffusion length dimension $D^2$. For mathematical treatment, $D^1$ will be designated as $l_\alpha$ while $D^2$ will be termed $\mu_s$. These entities can be defined by equations (1) and (2) in the attached formula sheet; $\lambda$ is the wave length of the light, $\alpha(\lambda)$ is the absorption coefficient of the sample at $\lambda$, $k_s$ is the thermal conductivity of the sample, $\rho_s$ is the sample's density, $C_s$ is the sample's specific heat, and $f$ is the modulation frequency of the light.

The absorption length $l_\alpha$ corresponds to the length along which most of the light is absorbed, and the thermal diffusion length $\mu_s$ corresponds to the depth beyond which the temperature fluctuations cannot reach the surface within the period defined by the light intensity fluctuations.

With strongly absorbing samples where the absorption length is much smaller than the sample thickness, say, typically by a factor of at least 10, two cases can be considered:

(a) $\mu_s \ll l_\alpha$: In this case, only that part of the light which is absorbed inside the thermal diffusion length contributes to the signal which, accordingly, is sensitive to variations in the absorption length $l_\alpha$. The sound wave amplitude can be defined by equation (3) of the formula sheet where $\gamma_g$ is the ratio of the specific heat values of the gas, $P_0$ the mean pressure, $P_1$ the light intensity, $T_0$ the mean temperature, $V_g$ the gas volume, and $\mu_g$ the thermal diffusion length of the gas. In this case, the sound wave amplitude is proportional to the absorption coefficient of the sample.

(b) $\mu_s \gg l_\alpha$: In this case, all absorbed energy contributes to the signal which then is independent of variations in the absorption length. The sound wave amplitude is given by equation (4) of the formula sheet.

It is possible to vary the thermal diffusion length simply by changing the modulation frequency of the light, in order to be in either case (a) or (b) because the thermal diffusion length $\mu_s$ is inversely proportional to the square root of the modulation frequency $f$ (equation 2).

Now, while spectroscopic measurement would seem to require case (a) for sensitivity to the absorption coefficient of the sample, the invention is predicated upon the discovery that it is possible to take advantage of case (b) and to use the sample itself as a reference so as to cancel out fluctuations of temperature, pressure, gas volume, laser intensity, or gas composition.

This, in turn, leads to the core teaching of the present invention, namely to modulate simultaneously the light beam used in GC-PAS at different sonic modulation frequencies, namely at least a higher one ($f_1$) at which the GC-PAS signal depends, in essence, upon the absorption coefficient of the sample (case (a)), and at least a lower one ($f_2$) at which it does not, in essence, depend upon the absorption coefficient of the sample (case (b)), and it has been found, according to the invention, that the ratio of the signal components at such differing frequencies is independent of the above mentioned parameters depending upon the specifics of the method, or apparatus, except the absorption by the substance of interest.

The GC-PAS signal can be considered to constitute the sum of the components at each frequency as shown in equation (7) of the formula sheet, $\delta P(f_1)$ being defined by equation 3 while $\delta P(f_2)$ is defined by equation (4). $Q_{f1}$ and $Q_{f1}$ are constants depending upon specifics of the system used, namely the way in which the light is chopped, and upon the response of the microphone used.

The ratio $R_{PA}$ of the GC-PAS signal components at $f_1$ and $f_2$ is defined by equation (5) of the attached formula sheet. Substitution of equations (3) and (4) in (5) yields equation (6) shown on the attached formula sheet as an expression for the ratio of the GC-PAS signals. This ratio is essentially independent of laser intensity, pressure, temperature, gas volume, and gas parameters and is, in essence, dependent only upon the absorption coefficient and the physical parameters of the sample.

Figure 2:
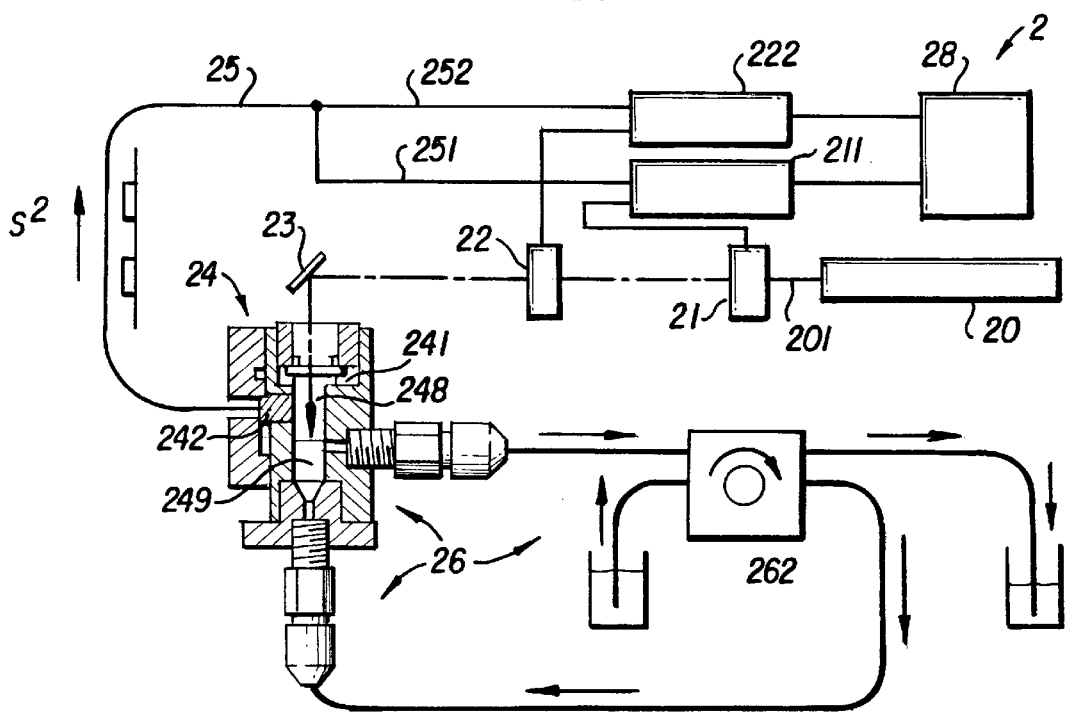
FIG. 2 is a diagrammatic illustration of an experimental setup used to operate the invention.

FIG. 2 illustrates an example of a laboratory apparatus 2 suitable for practicing the invention in accordance with the mathematical analyses explained above. A source 20 for monochromatic light, e.g. a $CO_2$ Laser, generates a beam 201 of light of a wavelength that corresponds to a high absorption band of the sample, e.g. glucose in aqueous solution for which the sample material produces a strong absorption, i.e. has at least one band of strong absorption.

Light beam 201 is modulated at two different frequencies, i.e. by a first modulating means, e.g. first chopper 21, generating a predetermined modulation of beam 201, and by at least one second modulating means, e.g. a second chopper 22, generating at least one other modulation of a differing frequency. Both choppers 21, 22 are frequency-stabilized electronically in a manner known per se, e.g. by circuitry inside the choppers (not shown in the drawing). Suitable choppers are available commercially, e.g. from Ithaco Corporation. Either the first or the second chopper could generate what has been termed the "primary" sonic modulation, i.e. the modulation which generates the signal depending both upon the absorption coefficient of the substance of interest and the parameters of operation, while the other, i.e. second or first chopper, would then cause the "secondary" sonic modulation of the beam, i.e. the modulation generating the signal that is not dependent upon the absorption coefficient of the substance of interest, but only upon the parameters of operation.

The sonic frequency of both modulators, e.g. choppers 21, 22, can be produced, for example, by a metallic motor-driven wheel or disc having peripheral recesses or "teeth". The number of teeth of the modulator generating the primary modulation is substantially higher than the number of teeth of the modulator generating the secondary signal; for example, the chopper for the primary modulation would have 27 teeth while the other chopper would have 2 teeth. The choppers or discs are operated at rotational speeds producing the desired primary and secondary modulation, respectively, e.g. 1800 rpm for the chopper with two teeth and 4400 rpm for the chopper with 27 teeth.

It is to be noted in this context that the examples given below are shown to operate with two modulation frequencies (2000 Hz for the primary modulation and 60 Hz for the secondary modulation) for easier understanding; however, the invention is not restricted to using only two different modulations but could use 4, 5, or more different modulations if the differences of the signals could be used to improve the quality of the measurement.

A mirror 23, e.g. a gold coated NiCu mirror, sends the doubly modulated laser beam into cell 24 made, for example, of stainless steel and provided with a window 241, e.g. made of ZnSe. A simple window heating (not shown in FIG. 2) consisting of a low-power resistor maintains the temperature of window 241 several degrees (e.g. about 10° C.) above the mean temperature in cell 24 to avoid any condensation which would absorb part of the incident light and produce a spurious GC-PAS signal. The microphone 242 provided in cell 24 should preferably be as small as possible so that the gas volume 248 can be minimized. This is of advantage because equations (3) and (4) indicate that the GC-PAS signal is inversely proportional to the gas volume.

Preferably, complicated geometries, such as narrow conduits connecting the cell portion containing the liquid sample 249 and the cell portion holding microphone 242 in contact with gas volume 248, should preferably be avoided when using the inventive method because they could create undesirable Helmholtz resonance that might negatively influence operation of the method and apparatus according to the invention.

Signal $S^2$ produced at the output of microphone 242 is then passed via line 25 into two branch lines 251, 252 for processing in lock-in devices 211, 222 which are externally locked by the reference frequencies coming from choppers 21,22.

Cell 24 is connected with an experimental sample passing system 26 suitable to simulate conditions of on-line operation. System 26 comprises a peristaltic two-way pump 262 to introduce, and simultaneously extract, a predetermined volume of sample liquid into and from cell 24. Acoustic insulation (not shown in FIG. 2) is provided in a manner known per se in the art of photoacoustic analyses, notably for excluding noise generated by pump 262, it being understood that use of such a pump need not be a feature of operation.

Apparatus 2 and the operation thereof is controlled by a data acquisition program of the type known per se and implemented in a conventional computing device 28 which records the signals coming from lock-ins 211, 222 as a function of time, and displays the GC-PAS signal amplitudes and phases at the primary and secondary modulation frequencies, as well as the ratio of the amplitudes.

Further, when setting the parameters of the two lock-ins 211,222, care should be taken that all parameters except the sensitivities should be set in the same manner, notably with regard to the time constants. Significant differences in the time constant settings would result in different time response of lock-ins 211,222 and alter the reference process. As for the sensitivities, each should preferably be set as high as possible for a given input signal, in order to lower the noise and to avoid non-linearity. Noise effects could also be reduced by choosing high time constants but this might slow down the time response of the system.

EXAMPLES

Specific examples of parameters for use in the apparatus and method according to the invention are given below by way of illustration and not of limitation. Percentages are by weight. Measurements were made at normal ambient conditions unless otherwise specified.

Example 1

A laboratory installation substantially as illustrated in FIG. 2 was used. Light source 20 was a $CO_2$ laser emitting at a wavelength of 9.676 $\mu$m with a power of about 1 W. The particular wavelength of 9.676 $\mu$m was selected because aqueous sucrose solution has a band of strong absorption in that region. The primary chopper 21 was operated to generate a primary modulation frequency of 2000 Hz while secondary chopper 22 was operated to generate a secondary modulation frequency of 60 Hz.

Cell 24 contains a gas volume of approximately 0.28 ml, and a liquid volume of 0.3 ml. The GC-PAS signal is measured by a simple commercial miniature KE4 Sennheiser microphone of 5 mm diameter.

Equations (1) and (2) were applied for pure water, as well as for a 20% solution of glucose in pure water, and a frequency of 9.676 $\mu$m giving the following results:
$l_\alpha \cong 20$ $\mu$m for pure water
$l_\alpha \cong 10$ $\mu$m for 200 g/liter glucose
$\mu_{water}=27$ $\mu$m at modulation frequency $f=60$ Hz
$\mu_{water}=4.7$ $\mu$m at modulation frequency $f=2000$ Hz.
The following values were used:
$k_{water}=0.585$ W/m.°K
$\rho_{water}=1000$ kg/m$^3$
$C_{water}=4180$ J/kg.°K.
The value of $\alpha$ (9.676 $\mu$m) was found to vary between ~500 cm$^{-1}$ for pure water and ~1000 cm$^{-1}$ for 200 g/liter aqueous sucrose solution.

Accordingly, with a chopper operation resulting in a secondary lower modulation of 60 Hz, the conditions of case (b) are met, while a chopper operation resulting in a primary modulation of 2000 Hz meets the conditions of case (a).

It should be emphasized that the results of this example are given for purposes of illustration only and provide but a rough approximation. For practical GC-PAS application, changes of the density and the thermal parameters of the specific solutions would be taken into account. Specifically, the spacing between the primary and the secondary modulation could be changed, e.g. using a primary modulation of 1500 Hz and a secondary modulation of 200 Hz. In general, the sensitivity for the substances tested tended to be higher with the larger spacing between modulation frequencies.

Example 2

In the manner explained in Example 1 and with the same apparatus, various test runs were performed at modulation frequencies of 60 Hz and 2000 Hz and with lock-in time constants of three seconds. Acquisition points were taken every two seconds.

In order to test the long-time stability of the inventive method an apparatus, data acquisition points were taken every two seconds during several hours, with pure water in the cell and no operation of pump 262.

Figure 3:
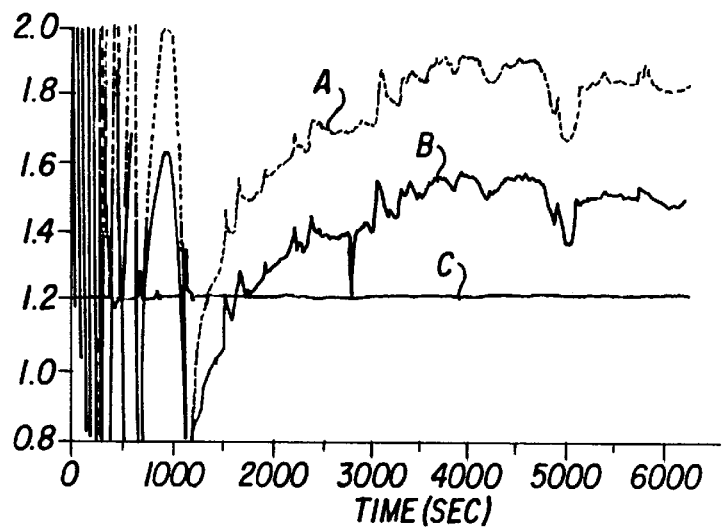
FIG. 3 is a diagram showing long time stability with pure water.
Figure 4:
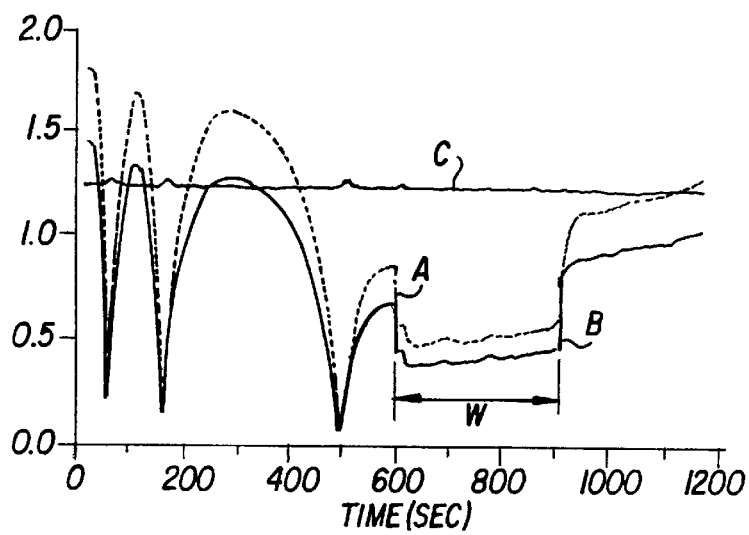
FIG. 4 is a diagram showing compensation of laser intensity fluctuations.

The results thus obtained are shown in the graph represented in FIG. 3 presenting (as also in FIGS. 4–7) the relative signal (in arbitrary units) on the ordinate and the time (in seconds) on the abscissa. Also, in FIG. 3 (and FIGS. 4–7 as well) the GC-PAS signal components at 60 Hz/10 mV (thin continuous line; indicated as B) and at 2000 Hz/0.1 mV (thin dotted line; indicated as A) as well as the signal ratio (thick continuous line; indicated as C) are displayed as a function of time. The GC-PAS signals at 60 Hz/10 mV and 2000 Hz/0.1 mV are proportional with the laser intensity of laser 20 which was operated without power stabilization. Except during an initial period of laser fluctuation following start-up, the signal ratio precision was about one percent.

Example 3

A further test run was made in the manner explained in Example 3 to demonstrate the effectiveness of the inventive method for compensating laser power fluctuations. The results are apparent from the graph shown in FIG. 4, again indicating the relative signal on the ordinate and the time (in seconds) on the abscissa. Again, line B indicates the 60 Hz/10 mV signal, A the 2000/0.1 mV signal and C the signal ratio.

During the first ten minutes, strong fluctuations of the laser intensity were observed and attributed to deformations of its cavity during the heating phase. Perturbations of the signal ratio appear near the lowest intensity points where the slope changes very rapidly, possibly due to minor differences in the response time of the lock-ins 211,222.

During the next four minutes (period length indicated as W), a ZnSe window was placed in front of the laser head in order to reflect back one part of the beam. A 30% attenuation of the laser intensity was thus produced simulating a substantial fluctuation of the laser intensity. As apparent from the graph of FIG. 4, the signal ratio (curve C) remained stable, however, within one percent.

Example 4

Figure 5:
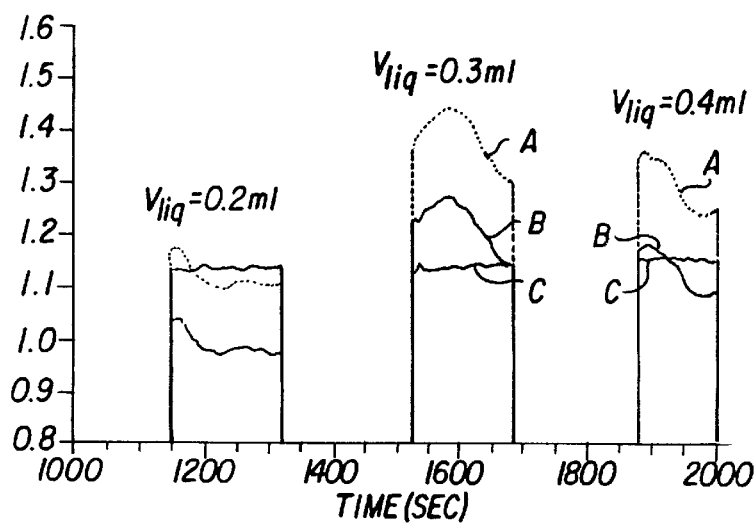
FIG. 5 is a diagram showing compensation of fluctuations of gas pressure and volume.
Figure 6:
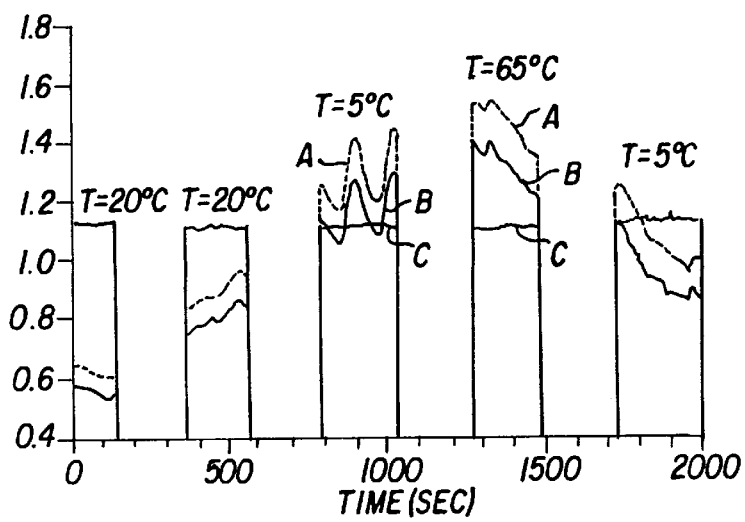
FIG. 6 is a diagram showing compensation of liquid temperature fluctuations in another example of the inventive method.

A further test-run was performed to test the effect of liquid temperature and of liquid level fluctuations. The apparatus was as used in the preceding examples. During operation of the apparatus, different amounts of water were injected into the cell. The signals measured as shown in FIG. 5. Data acquisition was stopped when the pump was operated so as to avoid low frequency noise.

As is apparent from FIG. 5, the signal ratios are the same for liquid amounts of 0.2, 0.3, and 0.4. The direct effect of the liquid level on the signal at 60 Hz and at 2000 Hz is not represented because of the instability of the laser intensity; this, however, confirms the usefulness of the present invention when operating with unstable laser sources. As is apparent from FIG. 6, the signal ratio was not perturbed when the liquid temperature was varied between 5° C. and 65° C.

Example 5

Figure 7:
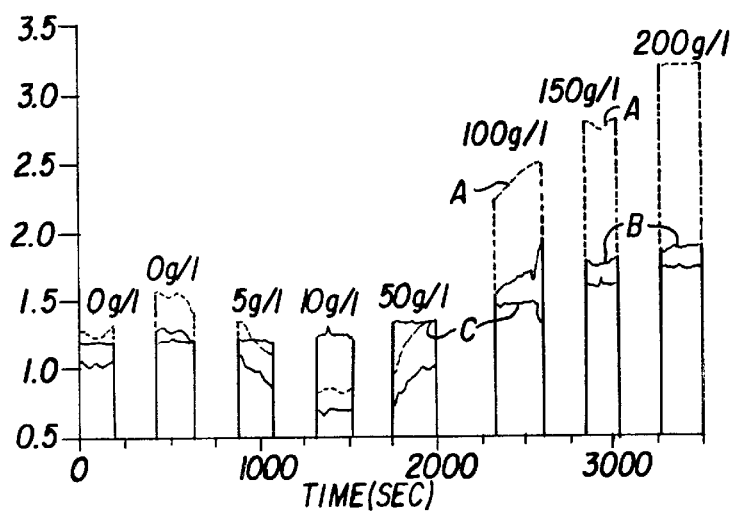
FIG. 7 is a diagram indicating time-dependent data acquisitions with various glucose concentrations.
Figure 8:
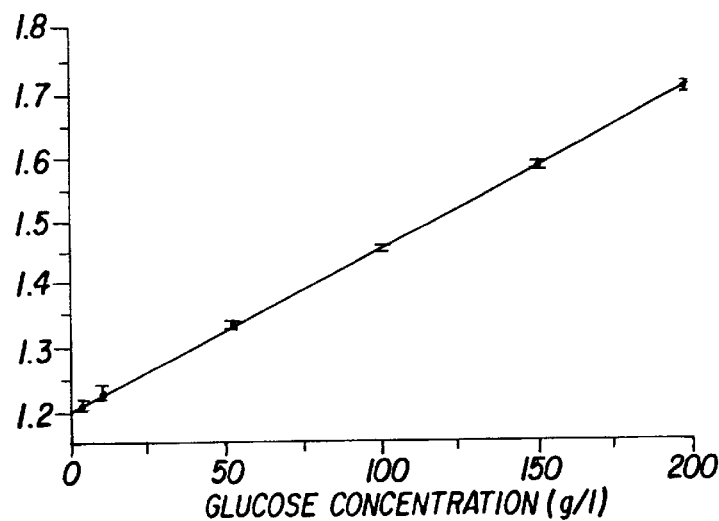
FIG. 8 is a diagram showing the signal ratio as a function of glucose concentration.

Using the apparatus shown in FIG. 2, aqueous solutions of glucose at concentrations ranging from 0 to 200 g/l were measured and an example of the results is shown in FIGS. 7 and 8. FIG. 7 represents the data acquisition including the GC-PAS signals at 60 Hz and at 2000 Hz, and the signal ratio. FIG. 8 shows the signal ratio as a function of glucose concentration. The signal ratio is linear for glucose concentrations ranging from 0 to 200 g/l.

Generally, it should be noted that since GC-PAS, per se, is a well known method of spectroscopy, many modifications of the above method and apparatus embodiments will be apparent to those experienced in the spectroscopic art. This applies both to the types of substances that are candidate materials for detection or monitoring according to the invention. Further, selection of suitable parameters for a given application of the present invention can be varied widely in view of specific conditions as long as the present teaching of sonic modification of the beam with at least two different modification means, such as choppers can be implemented. Notably, the invention could be adapted for operation with more than two beam modulation means producing more than two different modulations of the beam. Generally, the invention provides for more stable and precise results because of improved compensation of those parameters of operating GC-PAS analyses which are not dependent upon the substance of analytic interest.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A method for determining the concentration of a substance of interest by gas-coupled photoacoustic spectroscopy (GC-PAS) with an essentially monochromatic beam of radiation in an optical portion of the electromagnetic spectrum, said radiation being selected so as to be absorbed by the substance of interest and said beam being modulated at a primary sonic frequency which is sufficiently high for generating a signal (termed primary signal herein) that depends essentially upon the absorption coefficient of the substance of interest as well as upon parameters of operating the method, wherein:
   (a) the beam is additionally modulated at a secondary sonic frequency which is sufficiently low for generating an additional signal (termed secondary signal herein) which does not depend upon the absorption coefficient of the substance of interest, but depends only upon parameters of operating the method; and
   (b) forming a ratio of the primary and the secondary signals to generate a compensated signal for determining the concentration of the substance of interest.

2. The method of claim 1, wherein the monochromatic beam is modulated by periodic interruptions thereof, by physical or mechanical interruption, for obtaining the primary and the secondary signals.

3. The method of claim 1, wherein the substance of interest is a component of a liquid sample.

4. The method of claim 1, further comprising on-line measurements of the concentration of a substance of interest dissolved in a liquid.

5. The method of claim 1, further comprising on-line measurements of the concentration of a substance dissolved in a liquid.

6. The method of claim 1, wherein the monochromatic beam is modulated by choppers.

7. The method of claim 1, wherein the beam is modulated at the primary and secondary sonic frequencies simultaneously.

8. An apparatus for gas coupled photoacoustic spectroscopy (GC-PAS) suitable for determining the concentration of a substance of interest; said apparatus comprising:

(A) a source for producing at least one essentially monochromatic beam of a radiation in an optical portion of the electromagnetic spectrum; said radiation being selected so as to be absorbed by the substance of interest;

(B) a cell for receiving the substance of interest, said cell being operatively connected with a sonic detector for generating an output;

(C) means for modulation of the monochromatic beam at sonic frequencies;

(D) means for receiving the output from the sonic detector and for evaluating said output to produce a signal dependent upon the concentration of the substance of interest, characterized in that said means (C) for modulation comprises:

(C1) a first modulating means for imparting to the monochromatic beam at least one primary modulation frequency at which the output produced by the sonic detector is a primary signal dependent upon the absorption coefficient of the substance of interest and upon parameters of operating the apparatus, and (C2) a second modulating means for imparting to the monochromatic beam at least one secondary modulation frequency at which the output produced by the sonic detector is a secondary signal substantially not dependent upon the absorption coefficient of the substance of interest, but only upon the parameters of operating the apparatus;

and that said means (D) for receiving and evaluating include:

(D1) means for processing the output produced by the sonic detector so as to recover said primary signal and said secondary signal; and (D2) means for deriving, from a ratio between said primary signal and said secondary signal, a compensated signal that is dependent upon the absorption coefficient of the substance of interest, but not dependent upon the parameters of operating the apparatus.

9. The apparatus of claim 8, wherein both modulating means (C1, C2) are means for interrupting the beam by physical or mechanical means.

10. The apparatus of claim 9, wherein said modulating means are choppers.

11. The apparatus of claim 8, wherein said means (D1) for processing the output produced by the sonic detector and for recovering the primary signal and the secondary signal are lock-in amplifiers connected with the modulating means.

12. The apparatus of claim 8, further comprising means for passing a liquid stream through said cell.

13. The apparatus of claim 8, wherein the first and second modulating means impart to the monochromatic beam the primary and secondary modulation frequencies simultaneously.

* * * * *